United States Patent
Glynn et al.

(10) Patent No.: US 7,238,661 B2
(45) Date of Patent: Jul. 3, 2007

(54) ORAL LACTOFERRIN IN THE TREATMENT OF RESPIRATORY DISORDERS

(75) Inventors: Peter Glynn, Houston, TX (US); Atul Varadhachary, Houston, TX (US)

(73) Assignee: Agennix, Inc., Houston, TX (US)

( * ) Notice: Subject to any disclaimer, the term of this patent is extended or adjusted under 35 U.S.C. 154(b) by 338 days.

(21) Appl. No.: 10/441,329

(22) Filed: May 20, 2003

(65) Prior Publication Data

US 2004/0009896 A1   Jan. 15, 2004

Related U.S. Application Data

(60) Provisional application No. 60/410,645, filed on Sep. 13, 2002, provisional application No. 60/383,280, filed on May 24, 2002.

(51) Int. Cl.
*A61K 38/16* (2006.01)
*A61K 31/195* (2006.01)

(52) U.S. Cl. ........................... 514/6; 514/566

(58) Field of Classification Search ............ None
See application file for complete search history.

(56) References Cited

U.S. PATENT DOCUMENTS

| | | | |
|---|---|---|---|
| 4,977,137 A | 12/1990 | Nichols et al. | |
| 5,198,419 A | 3/1993 | Ando et al. | |
| 5,571,691 A | 11/1996 | Conneely et al. | |
| 5,571,697 A | 11/1996 | Conneely et al. | |
| 5,571,896 A | 11/1996 | Conneely et al. | |
| 5,676,930 A * | 10/1997 | Jager et al. | 424/45 |
| 5,766,939 A | 6/1998 | Conneely et al. | |
| 5,849,881 A | 12/1998 | Conneely et al. | |
| 5,916,900 A * | 6/1999 | Cupps et al. | 514/312 |
| 5,955,316 A | 9/1999 | Conneely et al. | |
| 6,080,559 A | 6/2000 | Conneely et al. | |
| 6,100,054 A | 8/2000 | Conneely et al. | |
| 6,111,081 A | 8/2000 | Conneely et al. | |
| 6,228,614 B1 | 5/2001 | Conneely et al. | |
| 6,399,570 B1 | 6/2002 | Mann | |
| 6,635,447 B1 | 10/2003 | Conneely et al. | |
| 2003/0105006 A1 | 6/2003 | Mann | |
| 2003/0190303 A1 | 10/2003 | Kimber et al. | |
| 2004/0009895 A1 | 1/2004 | Varadhachary et al. | |
| 2004/0082504 A1 | 4/2004 | Varadhachary et al. | |
| 2004/0142037 A1 | 7/2004 | Engel Mayer et al. | |
| 2005/0064546 A1 | 3/2005 | Conneely et al. | |
| 2005/0075277 A1 | 4/2005 | Varadhachary et al. | |

FOREIGN PATENT DOCUMENTS

WO    WO-9844940 A1   10/1998

OTHER PUBLICATIONS

Elrod et al, "Lactoferrin, a Potent Tryptase Inhibitor, Abolishes Late-Phase Airway Responses in Allergic Sheep," Am J Respir Crit care Med vol. 156, 1997, pp. 375-381.
Thomas et al, "Immobilized Lactoferrin is a Stimulus for Eosinophil Activation," The Journal of Immunology 2002, pp. 993-999.
Rice et al, "Inhibitors of Tryptase for the treatment of Mast Cell-Mediated Diseases," Current Pharmaceutical Design vol. 4, 1998, pp. 381-396.
U.S. Appl. No. 10/733,621, filed Dec. 11, 2003
U.S. Appl. No. 10/728,521, filed Dec. 5, 2003.
U.S. Appl. No. 10/862,213, filed Jun. 7, 2004.
U.S. Appl. No. 10/728,275, filed Dec. 4, 2003.
U.S. Appl. No. 10/844,865, filed Aug. 21, 2003.
U.S. Appl. No. 10/732,429, filed Dec. 9, 2003.

* cited by examiner

*Primary Examiner*—Zohreh A. Fay
(74) *Attorney, Agent, or Firm*—Fulbright & Jaworski LLP

(57) ABSTRACT

The present invention relates to methods of treating an allergic or non-allergic respiratory disorder by administering orally a composition of lactoferrin alone or in combination with metal chelators to treat respiratory disorders.

14 Claims, 9 Drawing Sheets

ORAL LACTOFERRIN IN THE TREATMENT OF RESPIRATORY DISORDERS

This application claims priority to U.S. Provisional Application No. 60/383,280, file May 24, 2002 and U.S. Provisional Application No. 60/410,645, filed Sep. 13, 2002, which are incorporated herein by reference in their entirety.

FIELD OF INVENTION

The present invention relates to methods of treating a respiratory disorder by administering orally a composition of lactoferrin (LF) alone or in combination with standard therapies or metal chelators, such as EDTA (ethylenediaminetetraacetic acid) to treat respiratory disorders. More particularly, the present invention relates to methods of treating allergic or inflammatory respiratory disease by administering orally a composition of lactoferrin alone, or in combination with standard therapies or a metal chelator. Still further, the present invention relates to methods of treating asthma by administering orally a composition of lactoferrin alone, or in combination with a metal chelator.

BACKGROUND OF THE INVENTION

Asthma is a very common disease in the United States and other industrialized countries, affecting more than 5% of the population. Key features of asthma are airway smooth muscle hyperreactivity, leading to variable airflow obstruction; infiltration of the airway wall with inflammatory cells, most notably helper T-cells ($Th_2$) lymphocytes and cosinophils; and structural changes, such as metaplasia of the airway epithelium from non-secretory ciliated cells to mucus-secreting goblet cells and thickening of the subepithelial basement membrane.

Most asthmatics have mild disease that is controlled with low doses of inhaled corticosteroids to suppress inflammation, and inhaled $\beta_2$-adrenoceptor agonists to relax airway smooth muscle. However, even low doses of inhaled steroids cause systemic side effects, such as growth suppression in children and cataracts in adults. Further, approximately 15% of asthmatics have severe disease that can lead to disability or death despite treatment with high doses of steroids. Thus, safer and more effective treatments for asthma are needed.

Lactoferrin is a single chain metal binding glycoprotein. Many cells types, such as monocytes, macrophages, lymphocytes, and brush-border cells, are known to have lactoferrin receptors. In addition to lactoferrin being an essential growth factor for both B and T lymphocytes, lactoferrin has a wide array of functions related to host primary defense mechanisms. For example, lactoferrin has been reported to activate natural killer (NK) cells, induce colony stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity.

EDTA (ethylenediaminetetraacetic acid) is a synthetic compound which has well known metal-binding characteristics. EDTA is most commonly used for chelation therapy, a treatment that involves repeated intravenous administration of EDTA to pull toxins from the bloodstream. EDTA administration is the medically accepted treatment for poisoning by heavy metals such as lead, mercury, arsenic and thallium and has been approved by the Food and Drug Administration (FDA) for this use.

EDTA has also been proposed as a treatment for heart disease. Proponents of chelation therapy for heart disease claim that EDTA, in combination with oral vitamins and minerals, helps dissolve plaques and mineral deposits associated with atherosclerosis. Although many Americans with heart disease have turned to EDTA chelation therapy to improve their condition, the FDA has not approved this therapy as an alternative treatment for heart disease. It is thought that EDTA chelation may help strengthen the immune system by sequestering impurities from the bloodstream. EDTA is not known to cause any significant side effects when administered orally to humans.

The present invention is the first to use an oral lactoferrin composition as a treatment for allergic respiratory disorders, such as asthma. Yet further, the present invention is the first to use lactoferrin in combination with a metal chelator to treat respiratory disorders, such as asthma.

BRIEF SUMMARY OF THE INVENTION

The present invention is directed to a method for treating respiratory disorders. The method of treatment involves oral administration of a lactoferrin composition alone or in combination with standard therapies or a metal chelator. The present invention is directed to a method for treating allergic or inflammatory respiratory disorders, including asthma.

An embodiment of the present invention is a method of treating a respiratory disorder comprising the step of administering orally to a subject a lactoferrin composition in an amount sufficient to provide an improvement in the respiratory disorder in the subject. The amount of lactoferrin composition that is administered is about 1 mg to about 10 g per day, more preferably 10 mg to 1 g. In specific embodiments, the lactoferrin composition is dispersed in a pharmaceutically acceptable carrier. More particularly, the lactoferrin is mammalian lactoferrin, for example human or bovine. Still further, the lactoferrin is recombinant lactoferrin. A further embodiment comprises administering an antacid in conjunction with said lactoferrin composition.

The respiratory disorder is allergic or non-allergic. More specifically, the respiratory disorder is selected from the group consisting of atopic asthma, non-atopic asthma, emphysema, bronchitis, chronic obstructive pulmonary disease, sinusitis and allergic rhinitis.

Still further, the lactoferrin composition may comprise a metal chelator dispersed in a pharmaceutically acceptable carrier. The metal chelator is ethylenediaminetetraacetic acid (EDTA), [ethylenebis (oxyethylenenitrilo)] tetraacetic acid (EGTA), 1,2-bis(2-aminophenoxy)ethane-N,N,N',N'-tetraacetic acid (BAPTA), hydroxyethlene triamine diacetic acid, (HEDTA). More specifically, the metal chelator is EDTA. The amount of EDTA that is administered is about 0.01 µg to about 20 g per day, preferably the ratio of EDTA to lactoferrin in the composition that is administered is from 1:10,000 to about 2:1.

Another embodiment of the present invention is a method of treating a respiratory disorder comprising the step of supplementing the mucosal immune system in a subject by increasing the amount of lactoferrin in the gastrointestinal tract. The lactoferrin is administered orally.

Still further, another embodiment is a method of enhancing a mucosal immune response in the gastrointestinal tract in a subject comprising the step of administering orally to the subject a lactoferrin composition. The lactoferrin stimulates interleukin-18 and Granulocyte Macrophage Colony Stimulating Factor (GM-CSF) in the gastrointestinal tract. IL-18 stimulates the production, maturation, migration or activity of immune cells, e.g., T lymphocytes or natural killer cells. T lymphocytes are selected from the group consisting of CD4+, CD8+ and CD3+ cells. GM-CSF also stimulates the production, maturation, migration or activity of immune cells, e.g., dendritic cells and other antigen presenting cells. Yet further, the lactoferrin reduces the production or activity of pro-inflammatory cytokines; reduces the infiltration of inflammatory cells into the lung; and reduces the delayed hypersensitivity associated with atopic or non-atopic asthma. Moreover, the lactoferrin composition can be administered in combination with an anti-asthma therapy selected from the group consisting of mast cell degranulation agents, leukotriene inhibitors, corticosteroids, beta-antagonists, IgE binding inhibitors, anti-CD23 antibody, tryptase inhibitors, and VIP agonists.

Another embodiment of the present invention is a method of treating a respiratory disorder comprising the step of administering orally to a subject a composition having lactoferrin and a metal chelator in an amount sufficient to provide an improvement in the respiratory disorder in the subject. The composition can be administered orally. Still further, the composition that is administered can be in a liquid formulation, a solid formulation with an enteric coating, or a solid formulation without an enteric coating.

In further embodiments, the lactoferrin composition can be administered in combination with a known agent to treat respiratory diseases. Known or standard agents or therapies that are used to treat respiratory diseases include, anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisterization by nebulization, anti-tussives, respiratory stimulants, surgery and alpha 1 antitrypsin.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
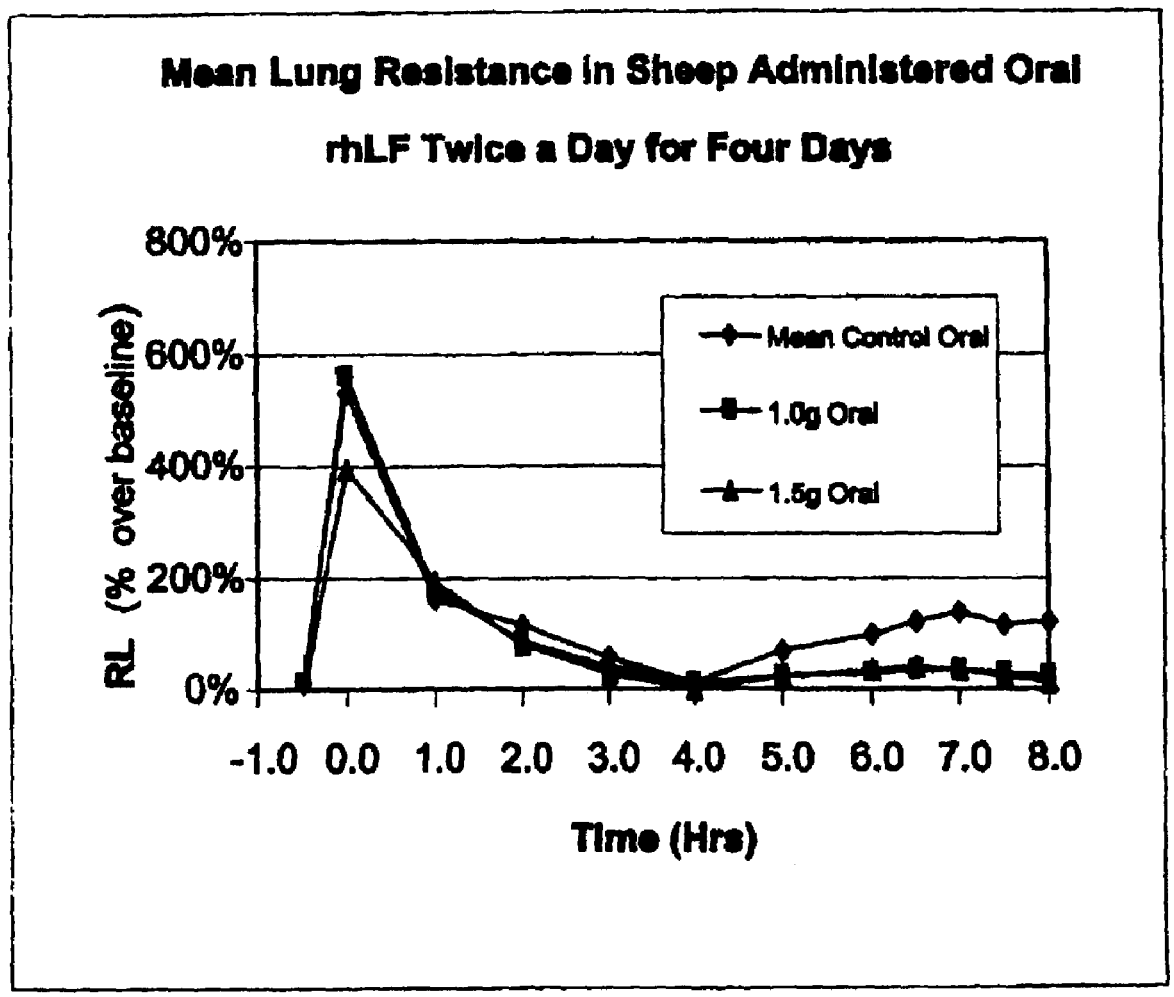
FIG. 1 shows lung resistance with or without oral administration of recombinant human lactoferrin administered twice a day for four days in sheep.
Figure 2:
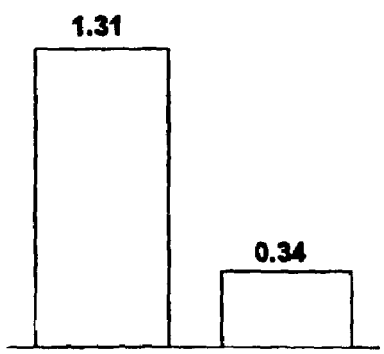
FIG. 2 shows the peak delayed increase in lung resistance with or without oral administration of recombinant human lactoferrin administered twice a day for four days in sheep.
Figure 3:
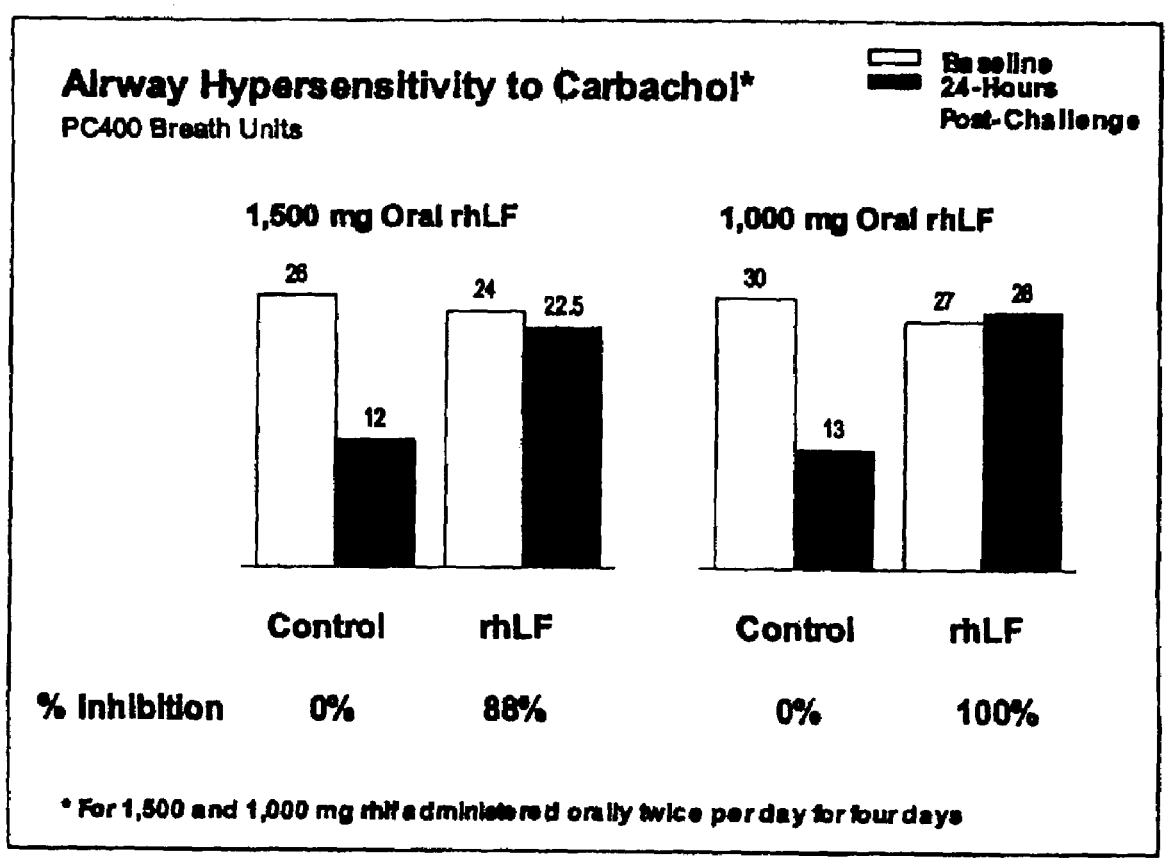
FIG. 3 shows delayed airway hypersensitivity as measured by resposne to carbachol, with or without oral administration of recombinant human lactoferrin administered twice a day for four days in sheep.
Figure 4:
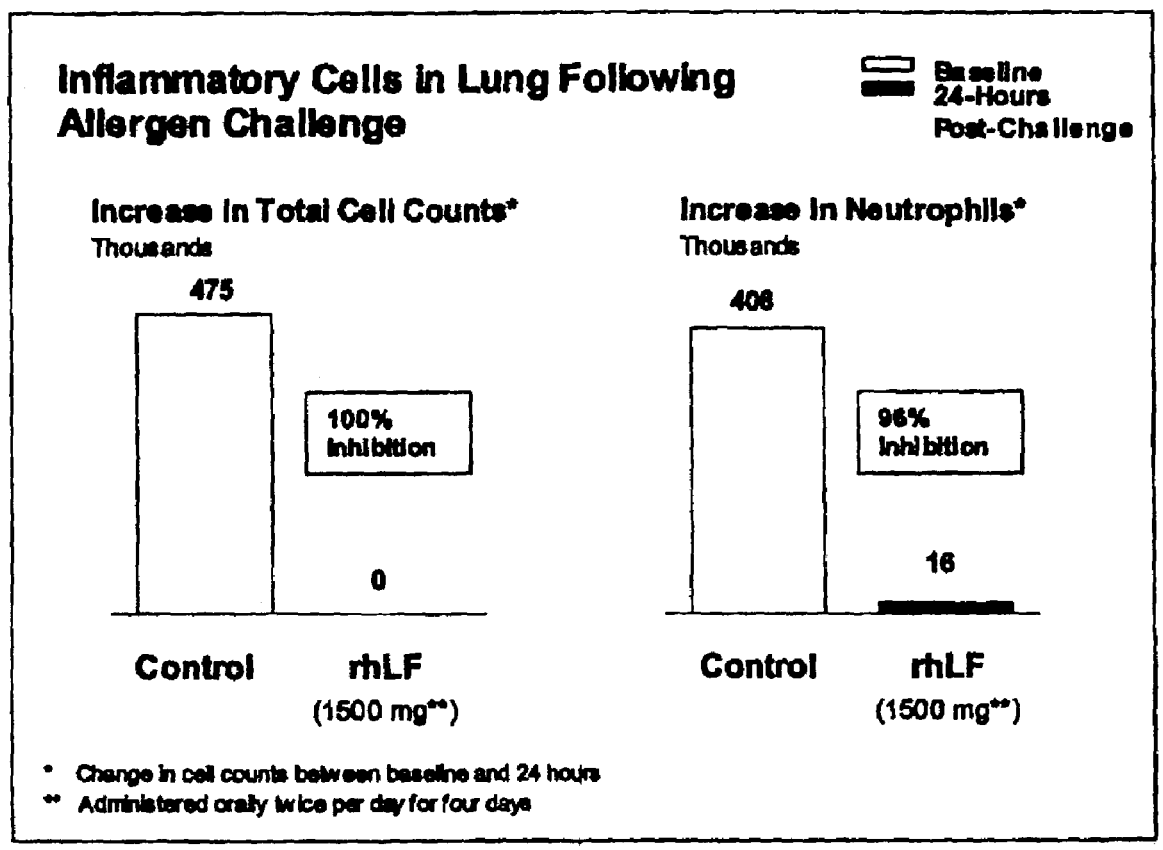
FIG. 4 shows the increase in inflammatory cells in the lung following allergen challenge with or without oral or inhaled—administration of recombinant human lactoferrin administered twice a day for four days in sheep.

It is readily apparent to one skilled in the art that various embodiments and modifications can be made to the invention disclosed in this Application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one."

The term "asthma" as used herein is defined as a disease of the airways that is characterized by increased responsiveness of the tracheobronchial tree to a multiplicity of stimuli.

The term "allergic respiratory disorder" or "hypersensitivity disease" refers to allergic diseases and/or disorders of the lungs or respiratory system. Allergic disorders are characterized by hypersensitivity to an allergen.

The term "atopic" as used herein refers to a state of atopy or allergy to an allergen or a state of hypersensitivity to an allergen. Typically, atopic refers to Type I hypersensitivity which results from release of mediators (e.g., histamine and/or leukotrines) from IgE-sensitized basophils and mast cells after contact with an antigen (allergen). An example of atopic is atopic asthma, which is allergic asthma and is characterized by an IgE response.

The term "allergen" as used herein refers to an innocuous antigen that induces an allergic or hypersensitive reaction.

The term "allergic rhinitis" as used herein is characterized by any of the following symptoms: obstruction of the nasal passages, conjuctival, nasal and pharyngeal itching, lacrimation, sneezing, or rhinorrhea. These symptoms usually occur in relationship to allergen exposure.

The term "hypersensitivity disease" refers to a condition in which the subject has an abnormal sensitivity to an innocuous agent, allergen. Hypersensivity disease can be categorized into four types, Type I, Type II, Type III and Type IV. Type I is described as atopic or anaphylactic which results from a release of mediators from IgE-sensitized basophils and mast cells. Type II is described as cytotoxic which involves complement-fixing antibody with cell lysis or antibody-dependent cellular cytotoxocity. Type III is described as immune-complex-mediated which is associated with soluble antigen-antibody complexes. Type IV is described as cell-mediated or delayed hypersensitivity which results from a release of lymphokines by sensitized T lymphocytes after contact with an antigen.

The term "lactoferrin" or "LF" as used herein refers to native or recombinant lactoferrin. Native lactoferrin can be obtained by purification from mammalian milk or colostrum or from other natural sources. Recombinant lactoferrin (rLF) or recombinant human lactoferrin (rhLF) can be made by recombinant expression or direct production in genetically altered animals, plants, fungi, bacteria, or other prokaryotic or eukaryotic species, or through chemical synthesis.

The term "metal chelator" as used herein refers to a compound which binds metal. Metal chelators that can be used in the present invention include the divalent metal chelators, for example, ethylenediaminetetraacetic acid (EDTA), [ethylenebis (oxyethylenenitrilo)] tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof.

The term "non-allegic" as used herein refers to a respiratory disorder that is not a result from or caused by an allergen. Thus, the non-allergic respiratory disorder is caused by other mechanisms not relating to hypersensitivity to air inocuous agent or allergen.

The term "oral administration" as used herein includes oral, buccal, enteral or intragastric administration.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "subject" as used herein, is taken to mean any mammalian subject to which a human lactoferrin composition is orally administered according to the methods described herein. In a specific embodiment, the methods of the present invention are employed to treat a human subject. Another embodiment includes treating a human subject suffering from an allergic respiratory disorder.

The term "respiratory disorder" refers to any condition and/or disorder relating to respiration and/or the respiratory system. The respiratory disorder can be an allergic or non-allergic respiratory disorder. More specifically, the respiratory disorder includes, but is not limited to atopic asthma, non-atopic asthma, emphysema, bronchitis, chronic obstructive pulmonary disease, sinusitis and allergic rhinitis.

The term "$Th_2$ cells" as used herein is defined as a subset of CD4 T-cells that are characterized by the cytokines they produce. These cells are mainly involved in stimulating B cells to produce antibody and are often called helper T-cells. It is also known that extracellular antigens tend to stimulate the production of $Th_2$ cells. Thus, as used herein, "$Th_2$ cells" is interchangeable with "helper T-cells".

The term "therapeutically effective amount" as used herein refers to an amount that results in an improvement or remediation of the symptoms of the disease or condition.

The term "treating" and "treatment" as used herein refers to administering to a subject a therapeutically effective amount of a recombinant human lactoferrin composition so that the subject has an improvement in the disease. The improvement is any improvement or remediation of the symptoms. The improvement is an observable or measurable improvement. Thus, one of skill in the art realizes that a treatment may improve the disease condition, but may not be a complete cure for the disease.

A. Pharmaceutical Compositions

The present invention is drawn to a composition comprising lactoferrin that is dispersed in a pharmaceutical carrier. Yet further, the composition comprises lactoferrin in combination with a metal chelator dispersed in a pharmaceutical carrier. Thus, the present invention is drawn to a lactoferrin composition with or without a metal chelator. One of skill in the art understands that both compositions (e.g., lactoferrin alone or lactoferrin in combination with a metal chelator) are within the scope of the present invention and can be used interchangeably depending upon the type of response that is desired. In preferred embodiments, the composition of the present invention comprises lactoferrin and a metal chelator. It is envisioned that the addition of a metal chelator to the lactoferrin composition enhances the sequestering of metal ions and thus strengthens the immune system.

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is human lactoferrin produced recombinantly using genetic engineering techniques well known and used in the art, such as recombinant expression or direct production in genetically altered animals, plants or eukaryotes, or chemical synthesis. See, i.e., U.S. Pat. Nos. 5,571,896; 5,571,697 and 5,571,691, which are herein incorporated by reference.

Metal chelators that can be used in the in combination with lactoferrin, include the divalent metal chelators, for example, ethylenediaminetetraacetic acid (EDTA), [ethylenebis(oxyethylenenitrilo)] tetraacetic acid (EGTA), 1,2-bis(2-aminophenoxy)ethane-N,N,N',N'-tetraacetic acid (BAPTA), hydroxyethlene triamine diacetic acid, (HEDTA) or any salts thereof. More preferrably, EDTA is used in combination with lactoferrin.

Further in accordance with the present invention, the inventive composition suitable for oral administration is provided in a pharmaceutically acceptable carrier with or without an inert diluent. The carrier should be assimilable or edible and includes liquid, semi-solid, i.e., pastes, or solid carriers. Except insofar as any conventional media, agent, diluent or carrier is detrimental to the recipient or to the therapeutic effectiveness of a lactoferrin preparation and/or the metal chelator contained therein, its use in an orally administrable lactoferrin and/or metal chelator for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, i.e., by solution, suspension, emulsification, admixture, encapsulation, microencapsulation, absorption and the like. Such procedures are routine for those skilled in the art.

In a specific embodiment of the present invention, the composition in powder form is combined or mixed thoroughly with a semi-solid or solid carrier. The mixing can be carried out in any convenient manner such as grinding. Stabilizing agents can be also added in the mixing process in order to protect the composition from loss of therapeutic activity through, i.e., denaturation in the stomach. Examples of stabilizers for use in an orally administrable composition include buffers, antagonists to the secretion of stomach acids, amino acids such as glycine and lysine, carbohydrates such as dextrose, mannose, galactose, fructose, lactose, sucrose, maltose, sorbitol, mannitol, etc., proteolytic enzyme inhibitors, and the like.

Further, the composition which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, i.e., U.S. Pat. No. 5,629,001. Upon reaching the small intestines, the basic pH therein dissolves the coating and permits the composition to be released and absorbed by specialized cells, i.e., epithelial enterocytes and Peyer's patch M cells.

In another embodiment, a composition is combined with a liquid carrier such as, i.e., water or a saline solution, with or without a stabilizing agent.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

B. Treatment of Respiratory Disorders

In accordance with the present invention, the composition provided in any of the above-described pharmaceutical carriers is orally administered to a subject suspected of or having a respiratory disorder. The respiratory disorder can be an allergic or non-allergic respiratory disorder. One of skill in the art can determine the therapeutically effective amount of the composition to be administered to a subject based upon several considerations, such as local effects, pharmacodynamics, absorption, metabolism, method of delivery, age, weight, disease severity and response to the therapy. Oral administration of the composition includes oral, buccal, enteral or intragastric administration. It is also envisioned that the composition may be used as a food additive. For example, the composition is sprinkled on food or added to a liquid prior to ingestion.

In further embodiments, the composition is administered in conjunction with an antacid. Thus, an antacid is administered prior or substantially simultaneously with or after oral administration of the composition. The administration of an antacid just prior or immediately following the administration of the composition may help to reduce the degree of inactivation of the lactoferrin in the digestive tract. Examples of appropriate antacids include, but are not limited to, sodium bicarbonate, magnesium oxide, magnesium hydroxide, calcium carbonate, magnesium trisilicate, magnesium carbonate and alumin hydroxide gel.

According to the invention, an allergic or non-allergic respiratory disorder includes asthma, emphysema, bronchitis, chronic obstructive pulmonary disease, sinusitis and allergic rhinitis. In specific embodiments, the respiratory disorder is characterized by increased responsiveness of the trachea and bronchi to various stimuli, i.e., allergens, resulting in widespread narrowing of the airways.

In a preferred embodiment of the present invention, the composition is administered in an effective amount to decrease, reduce, inhibit or abrogate the obstruction of the airway or the hyperresponsiveness of the respiratory system to the allergen or other stimuli. The amount of lactoferrin in the composition may vary from about 1 mg to about 100 g. Preferably, the composition that is orally administered contains the range of 1 mg to 10 g of lactoferrin per day, more preferably, 10 mg to about 1 g. More preferably, the composition of the present invention also contains metal chelators, for example, but not limited to ethylenediaminetetraacetic acid (EDTA), [ethylenebis (oxyethylenenitrilo)] tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof. The amount of the metal chelator in the composition may vary from about 0.01 µg to about 20 g. A preferred metal chelator is EDTA. More preferably, the composition that is orally administered contains the ratio of 1:10,000 to about 2:1 EDTA to lactoferrin.

Treatment regimens may vary as well, and often depend on the respiratory disease, such as the specific asthma type, health and age of the patient. Obviously, certain types of asthma will require more aggressive treatment, while at the same time, certain patients cannot tolerate more taxing regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. In a further embodiment, the lactoferrin is given in a series of doses. The series of doses may be administered daily, or multiple times a day, weekly, or multiple times a week, or monthly, or multiple times a month.

A further embodiment of the present invention is a method of treating an allergic or non-allergic respiratory disorder comprising the step of supplementing a mucosal immune system by increasing the amount of lactoferrin in the gastrointestinal tract. Preferably, the lactoferrin is administered orally.

Still yet, a further embodiment is a method of enhancing a mucosal immune response in the gastrointestinal tract in a subject comprising the step of administering orally to said subject the composition of the present invention. The composition contains lactoferrin alone or in combination with a metal chelator, such as EDTA. The lactoferrin stimulates interleukin-18 and/or GM-CSF in the gastrointestinal tract, which enhances the immune resposne. IL-18 stimulates the production, maturation, migration or activity of immune cells, e.g., T lymphocytes or natural killer cells. T lymphocytes are selected from the group consisting of CD4+, CD8+ and CD3+ cells. GM-CSF also stimulates the production, maturation, migration or activity of immune cells, e.g., dendritic cells and other antigen presenting cells. It is known by those of skill in the art that IL-18 is a $Th_1$ cytokine that acts in synergy with interleukin-12 and interleukin-2 in the stimulation of lymphocyte IFN-gamma production. Other cytokines may also be enhanced for example, but not limited to IL-1, IL-2, IL-10, IL-12 or IFN-gamma. It is also envisioned that lactoferrin stimulates interleukin-18 following oral administration, which inhibits pro-inflammatory cytokines, i.e., IL-4, IL-5, IL-6, IL-8 and TNF-alpha.

In further embodiments, it is envisioned that oral administration of lactoferrin stimulates IL-18 in the lungs, sinuses or systemically. Yet further, it is contemplated that an enhancement of lactoferrin can reduce the infiltration of inflammatory cells into the lung.

Yet further, it is envisioned that oral administration of lactoferrin in combination with a metal chelator, such as EDTA, enhances the amount of metal ion that is sequestered and therefore strengthens and/or enhances the immune system.

C. Combination Treatments

In order to increase the effectiveness of oral administration of the composition of the present invention, it is desirable to combine these compositions with an additional agent. For example, known asthma agents are used in combination with the composition of the present invention. Exemplary agents known to treat asthma include mast cell degranulation agents (i.e., Cromylyn sodium or Nedocromil sodium), leukotriene inhibitors (i.e., Monteleukast sodium, Zafirlukast, or Pranlukast hydrate), corticosteroids (i.e., Beclomethasone, Budesonide, Ciclesonide, Hydrolysable glucocorticoid, Triamcinolone acetonide, Flunisolide, Mometasone furoate, or Fluticasone propionate), β-Antagonists (i.e., Albuterol, Bambuterol, Formoterol, Salbutamol, Terbutaline sulfate, or Salmeterol), IgE binding inhibitors (i.e., Omalizumab), Adenosine A2 agonists, Anti-CD23 antibody, E-Selectin antagonists, P-Selectin antagonists, L-Selectin antagonists, interlukin inhibitors/monoclonal antibodies, pulmonary surfactants, neurokinin antagonists, NF-Kappa-B inhibitors, PDE-4 inhibitors (i.e., Cilomilast, or Roflumilast), Thromboxan A2 inhibitors (i.e., Ramatroban, or Seratrodast), tryptase inhibitors, VIP agonists or antisense agents.

Yet further, the agent is a known agent used to treat allergic rhinitis. Exemplary agents include, but are not limited to H1 antihistamines i.e., terfendine or astemizole; alpha-adrenergic agents; and glucocorticoids, i.e., beclamethasone or flunisolide.

In addition, the agent is a known agent to treat sinusitis, more specifically, chronic sinusitis. Exemplary agents/therpies include, but are not limited to surgery (e.g., enlarging a sinus passage, remove obstructing bone or nasal polyps, mucosal stripping, removal of sinuses); corticosteroids (e.g., oral, intranasal, nebulized, or inhaled); antibiotics (e.g., oral, intranasal, nebulized, inhaled or intravenous); anti-fungal agents; salt-water nasal washes and mist sprays; anti-inflammatory agents; decongestants (oral or nasal); guaifenesin; potassium iodide; leukotriene inhibitors (e.g., monteleukast); mast cell degranulating agents; topical moisterizing applications (e.g., nasal sprays or gels which may contain moisterizing agents such as propylene glycol or glycerin); hot air inhalation; mechanical devices to aid in breathing; enzymatic cleansers (e.g., papaya enzymes); and antihistame sprays.

Still further, the agent is a known agent to treat COPD or chronic bronchitis or emphysema. Exemplary agents/interventions include, but are not limited to oxygen; bronchodilator drugs [e.g., short and long acting beta-2 stimulants, anticholinergics (e.g., ipratoprium bromide, theophylline compounds or a combination), steroids (topical or oral), or mucolytic agents (e.g., ambroxol, ergosterin, carbocysteine, iodinated glycerol)]; antibiotics; anti-fungals; moisterization by nebulization; anti-tussives; respiratory stimulants (e.g., doxapram, almitrine bismesylate); surgery (e.g., bullectomy, lung volume reduction surgery, lung transplantation); and alpha 1 antitrypsin administration.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Multiple Day Oral Administration to Sheep

Allergic sheep were treated with rhLF and compared to their historic controls. Baseline bronchoalveolar lavage fluid (BAL) samples were taken from all animals and baseline dose response curves to aerosol carbachol were obtained in all sheep 1-3 days before the start of dosing. Afterward, sheep were pre-treated with oral rhLF in doses of 1.0 g or 1.5 g, twice daily for 3 days prior to allergen challenge. Plasma samples (2 ml) were taken from the two sheep receiving rhLF at both the time of 1st dose on day 1 and again on day 3 at the time of the second daily dose.

On the challenge day (day 4) the active sheep received 1.0 g or a 1.5 g doses of rhLF 30 min before, 4 h after and 24 h after allergen challenge. BAL samples were again taken from all sheep 8-9 hours after allergen challenge and again 24 hours after antigen challenge. Additional plasma samples were taken from the active sheep before and immediately after rhLF administration, immediately before and after antigen challenge, and then at intervals of 15, 30, 60, 180 minutes and at 6, 7.5, 9 and 24 hours after allergen challenge.

On the challenge day (day 4) measurements of lung resistance (RL) were obtained before and then repeated 30 min after treatment and then the sheep were challenged with *Ascaris suum* allergen using an esophageal balloon catheter (Abraham et al., 1983). Measurements of RL were obtained immediately after challenge, hourly from 1-6 h after challenge and on the half-hour from 6 ½-8 h after challenge. Measurements of RL were obtained 24 h after challenge followed by the 24 h post challenge dose response curve. Airway responsiveness, defined as the cumulative carbachol dose required to increase RL by 400% (Abraham et al., 1983) was measured subsequent to the final dose of rhLF or vehicle. Airway resistance of each treated sheep was compared with the control (animal that only received vehicle).

FIG. 1, FIG. 2, FIG. 3 and FIG. 4 show that oral administration of rhLF inhibited the late response, airway hypersensitivity, and infiltration of eosinophils and other inflammatory cells into the airways.

Example 2

Oral Administration of rhLF

Oral rhLF at doses of 1000 mg or 1500 mg doses was administered twice daily for 3 days to sheep and compared to pre-treatment historical controls. On day 3, rhLF was administered in the morning a half hour prior to allergen challenge, four hours after allergen challenge and the next morning (prior to the carbachol challenge test to measure airway hypersensitivity). Both doses significantly blocked RL and AH with no dose dependence.

Figure 5:
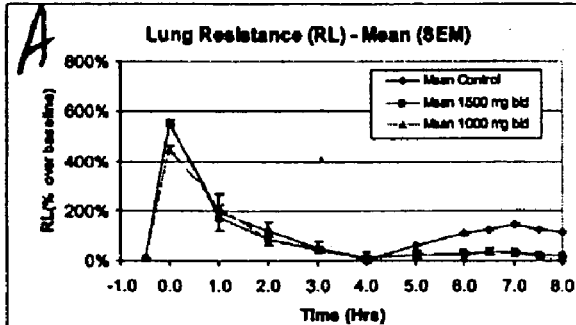
FIG. 5A and FIG. 5B show the lung resistance (FIG. 5A) and the delayed airway-hypersensitivity (FIG. 5B) with or without oral administration of recombinant human lactoferrin administered twice daily for three days in sheep.
Figure 5:
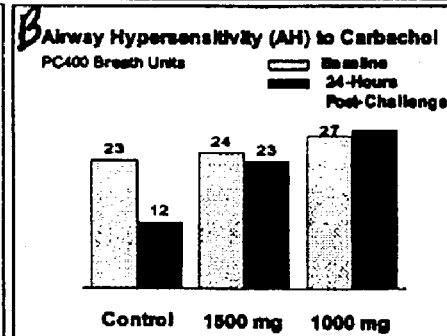

FIG. 5A and FIG. 5B show that RL and AH were inhibited by an average of 75% and 94% respectively (p<0.01).

Example 3

Once Daily Oral Administration to Sheep

Allergic sheep were treated with rhLF and compared to their historic controls. Baseline dose response curves to aerosol carbachol were obtained 1-3 days before the start of dosing. Afterward, sheep were pre-treated with oral rhLF in the dose of 1500 mg or 1000 mg, once daily for 3 days prior to allergen challenge with the dose being administered in the evening.

On day 3, the allergen challenge was performed in the morning (at lease 15 hours after last dose of RHLF). RhLF was administered again 8 hours after allergen challenge. On the morning of day 4, 24 hours after the allergen challenge, the carbachol challenge test (to measure airway hypersensitivity) was performed. Both doses significantly blocked RL and AH with no dose dependence and no loss in efficacy compared to the twice daily regimen used in Example 1 and Example 2.

Figure 6:
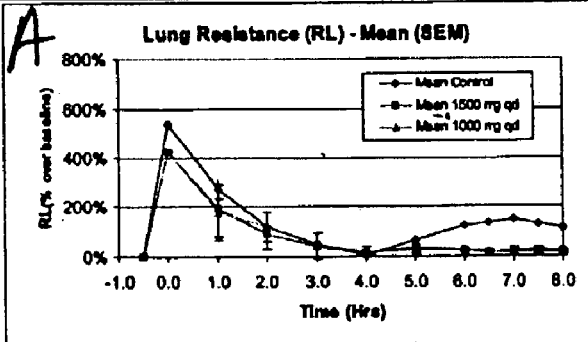
FIG. 6A and FIG. 6B show the lung resistance (FIG. 6A) and the delayed airway-hypersensitivity (FIG. 6B) with or without oral administration of recombinant human lactoferrin administered once daily for three days in sheep.
Figure 6:
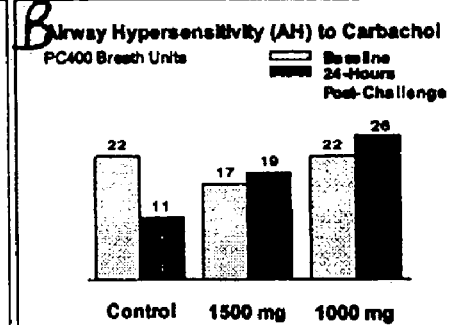

FIG. 6A and FIG. 6B show that a single daily dose of orally administered rhLF inhibited RL and AH by an average of 78% and 100% respectively (p<0.01).

Example 4

Evaluation of Longterm Treatment with rhLF

RhLF was administered at a dose of 1.5 g once daily for 28 days and the response to allergen and the delayed hypersensitivity was tested on Day 14 and Day 28 following the completion of rhLF dosing.

Figure 7:
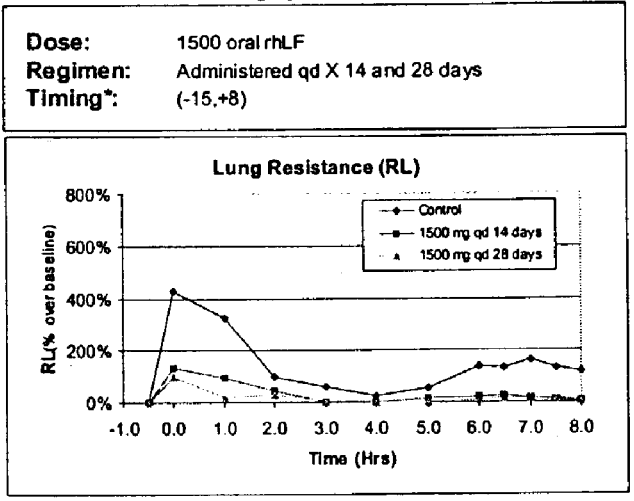
FIG. 7A and FIG. 7B show the lung resistance (FIG. 7A) and the delayed airway-hypersensitivity (FIG. 7B) with or without oral administration of recombinant human lactoferrin administered once daily for 14 days and 28 days in sheep.
Figure 7:
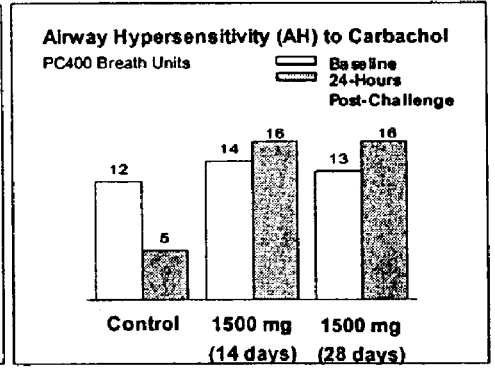
Figure 8:
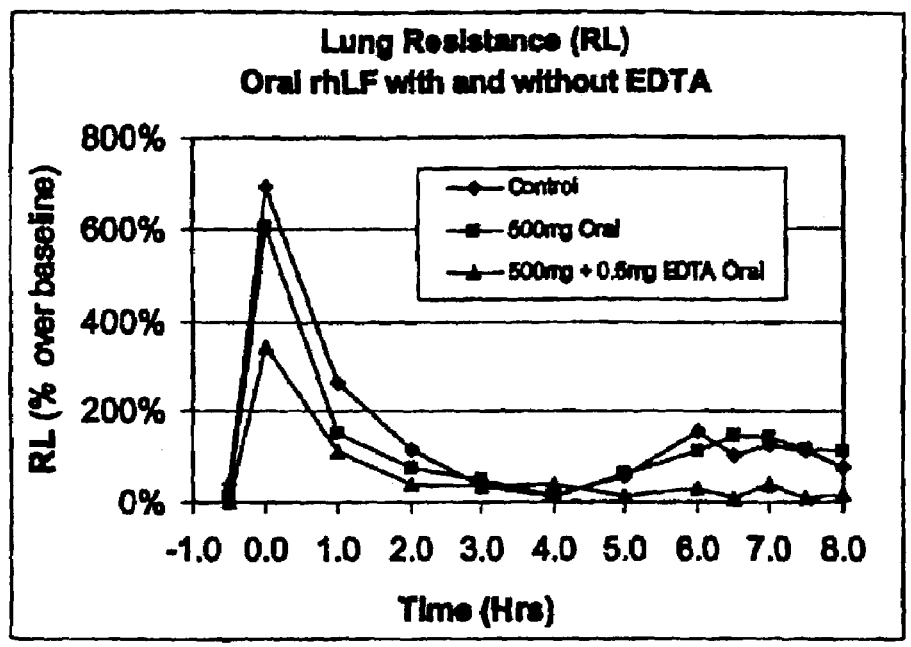
FIG. 8 shows lung resistance for oral administration of recombinant human lactoferrin once daily for 3 days with and without EDTA in sheep.
Figure 9:
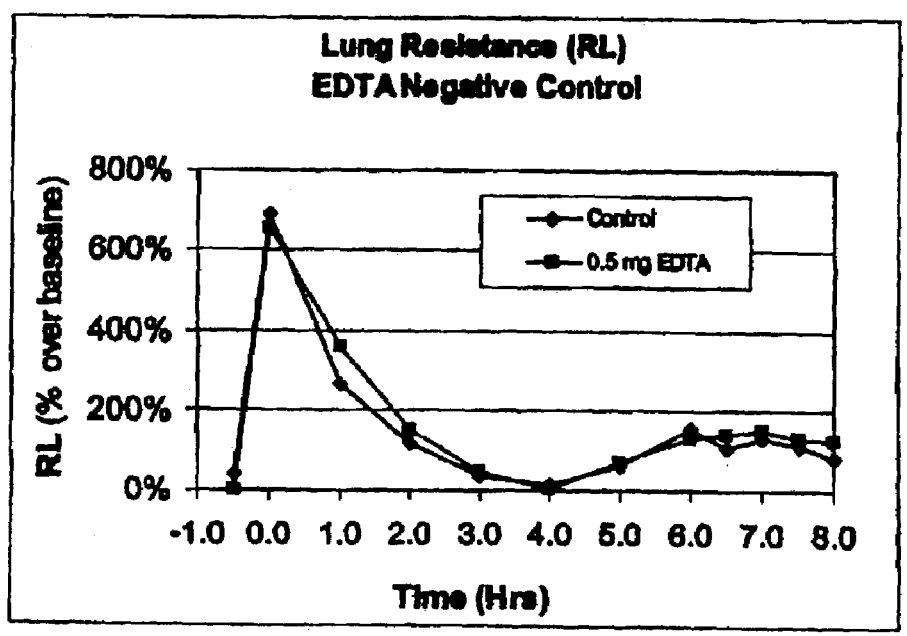
FIG. 9 shows lung resistance (RL) for oral administration EDTA alone once daily for 3 days as a negative control in sheep.
Figure 10:
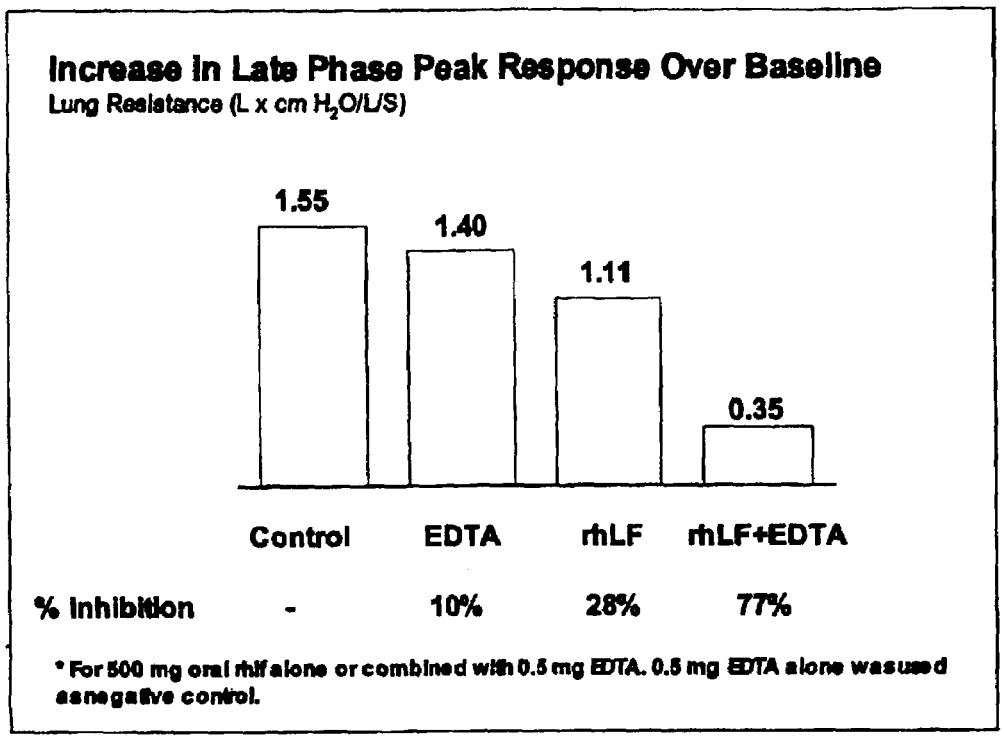
FIG. 10 shows the peak delayed increase in lung resistance for oral administration of recombinant human lactoferrin with and without EDTA in sheep.
Figure 11:
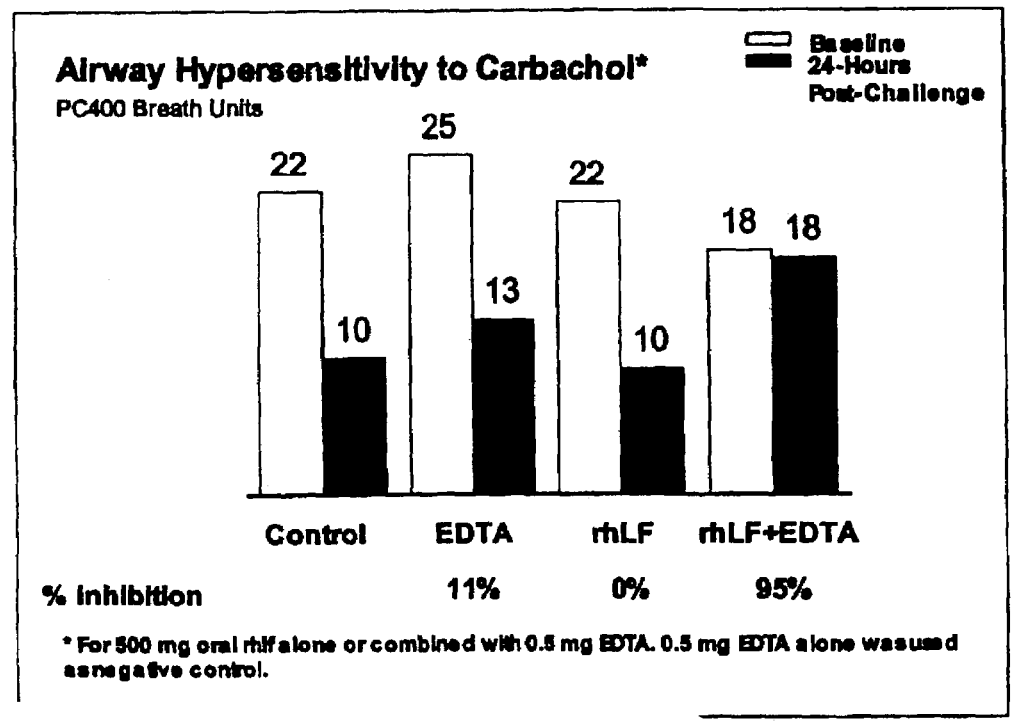
FIG. 11 shows delayed airway hypersensitivity for oral administration of recombinant human lactoferrin once daily for 3 days with and without EDTA in sheep.

As expected, rhLF's protective effect was not attenuated with continued administration. In fact, long-term rhLF administration unexpectedly provided protection against the early airway response (EAR; an effect not observed with shorter regimens) as well as enhanced protection against the late airway response. After 28 days, rhLF provided a 77% protection against the EAR in addition to a 90% and 100% protection against the late response and airway hypersensitivity respectively (FIG. 7A and FIG. 7B).

Example 5

Optimization of Administration of LF

Recombinant human lactoferrin, bovine lactoferrin and native human lactoferrin are orally administered to animals, and the production of IL-18, IL-1, IL-2, IL-4, IL-5, IL-10, IL-12 and IFN-gamma in the plasma, serum and blood packed cells are measured.

Briefly, the experimental protocol in Example 1 is used to determine the maximum duration of the protective effect of oral administration of rhLF.

Yet further, rhLF is administered for a period of time, such as days to weeks, followed by a gap of 1 day, 2 days, 3 days, a week, etc., to measure the duration of protection following stoppage of rhLF administration.

Briefly, animals receive 0.1, 0.5, 1.5, and 4.5 g doses of rhLF 4 hours, 12 hours, 24 hours, 2 days, 3 days, 4 days, 7 days and 14 days prior to allergen challenge. Plasma samples are taken from the animals before and immediately after lactoferrin administration, immediately before and after allergen challenge, and then at intervals of 4, 6, 9, 24, 36, 48, 79, etc., hours after allergen challenge. Immediate and late phase airway resistance, delayed hypersensitivity and BAL cellularity are measured as established in Example 1 at the given intervals. The levels of CD4+, CD8+ and NK cells are counted from the blood that was collected. Plasma, serum and an extract of the blood cells are used for cytokine ELISA assays, i.e., IL-18, IL-1, IL-2, IL-4, IL-5, IL-10, IL-12 and IFN-gamma.

Example 6

Combination Treatments of LF and Anti-asthma Agents

Animals (sheep, rodents, dogs or primates) are administered standard or published anti-asthma regimens with or without the addition of oral rhLF administered using regimens identified as being optimal in the trials described in Example 5. Anti-asthma therapy is administered using standard or published regimens.

The efficacy of individual and combination treatments are evaluated by measuring immediate and late phase airway resistance, and delayed hypersensitivity and BAL cellularity as described in Example 1. Yet further, the levels of CD4+, CD8+ and NK cells are counted from the blood that was collected. Plasma, serum and an extract of the blood cells are used for cytokine ELISA assays, i.e., IL-18, IL-1, IL-2, IL-4, IL-5, IL-10, IL-12 and IFN-gamma.

Example 7

Combination Treatments of LF and Anti-allergic Rhinitis and Anti-sinusitis Agents Animals (sheep, rodents, dogs or primates) are administered standard or published anti-rhinitis and anti-sinusitis regimens with or without the addition of oral rhLF. rhLF is administered using regimens identified as being optimal in the trials described in Example 5. Anti-allergic rhinitis or anti-sinusitis therapy is administered using standard or published regimens.

The efficacy of individual and combination treatments are evaluated by measuring immediate and late phase airway resistance, and delayed hypersensitivity and BAL cellularity as described in Example 1. Yet further, the levels of CD4+, CD8+ and NK cells are counted from the blood that was collected. Plasma, serum and an extract of the blood cells are used for cytokine ELISA assays, i.e., IL-18, IL-1, IL-2, IL-4, IL-5, IL-10, IL-12 and IFN-gamma.

Example 8

Allergen Challenge Clinical Trials in Atopic Volunteers

Atopic patients with a documented response to the allergen were enrolled in a challenge trial. Patients had mild or moderate asthma and were free of other cardio-respiratory illnesses that may interfere with either the safety or the measurement of the early or late asthmatic responses.

Baseline measures of pulmonary function, including $FEV_1$ at 5, 10 and 15 minutes were made before and after inhalation of saline. Baseline allergen response was obtained by administering increasing amounts of known allergen until a fall in $FEV_1$ of 25% was observed. $FEV_1$ was measured at the following times post-allergen inhalation: 20, 30, 45 and 60 minutes. Following this, measurements were made at hourly intervals up to 4 hours, and then every 30 minutes up to 9 hours to untreated allergic response.

The baseline measurement was repeated two weeks after the first measurement.

After a further two weeks, rhLF was administered once a day in doses of 0.1, 0.5, 1.5, 3.0 and 4.5 g/day for three days. On the fourth day, a baseline $FEV_1$ was measured prior to allergen exposure. Two hours following the rhLF dose, allergen was administered to the patient in an amount required to decrease the $FEV_1$ by 25%. $FEV_1$ was measured at the following times post-allergen inhalation: 20, 30, 45 and 60 minutes. Following this, measurements were made at hourly intervals up to 4 hours, and then every 30 minutes up to 9 hours to untreated allergic response.

Blood was collected from the patients at baseline and daily for fourteen days following the start of rhLF administration to measure circulating CD4+, CD8+, and NK cells, NK cell activity and serum cytokines including IL-1, IL-2, IL-4, IL-5, IL-8, IL-10, IL-12, IL-18 and IFN-gamma.

Table 1 shows that in the 4 patients rhLF inhibited the peak early response following allergen challenge by an average 60%. Pre- and post-treatment measurements of $FEV_1$ at a constant cumulative dose of allergen were recorded in the first 30 minutes following allergen challenge and compared for each patient.

TABLE 1

| Patient | Cumm Allergen (SQ U/ml) | Baseline Allergen Challenge | | | Active Allergen Challenge | | | EAR Inhibition |
|---|---|---|---|---|---|---|---|---|
| | | Post Saline Value | Value for calc | % Change FEV | Post Saline Value | Value for calc | % Change FEV | |
| 4 | 21,250 | 3.55 | 2.47 | −30.4% | 3.30 | 2.80 | −15.2% | 50% |
| 6 | 5,250 | 4.20 | 3.30 | −21.5% | 4.31 | 4.10 | −4.9% | 77% |
| 09* | 13,250 | 3.50 | 2.79 | −20.3% | 3.72 | 3.00 | −19.4% | 5% |
| 13 | 5,250 | 3.94 | 2.82 | −28.4% | 4.27 | 4.23 | −0.9% | 97% |
| Average | | | | −25.1% | | | −10.1% | −59.9% |
| Adjusted Average** | | | | −26.8% | | | −7.0% | −73.9% |

*Patent was non-compliant with dosing
**Non-compliant patient excluded from average In response to allergen challenge, rhLF provided substantial protection against allergen sensitivity as measured by the provocative concentration of allergen required to produce a 25% drop in $FEV_1$ ($PC_{25}$ Allergen). Patients were challenged before and after treatment with rhLF. The allergen was administered in increasing incremental doses every 10 minutes until a 25% drop in $FEV_1$ was observed. Protective effect was defined as achieving an increase of at least 1 doubling-dose concentration of allergen to produce a 25% drop in $FEV_1$ post-treatment. The results presented in Table 2, demonstrate that rhLF provideed substantial protection against allergen sensitivity after 3 days of drug treatment.

TABLE 2

| | Allergen Administered (SQ-U) | |
|---|---|---|
| Patient | Pre-Treatment | Post-Treatment |
| 4 | 2.6 | 947.4 |
| 6 | 112.3 | 3,665.4 |
| 09* | 358.6 | 335.3 |
| 13 | 77.0 | 620.2 |
| Average | 137.6 | 1,392.1 |

*Patent was non-compliant with dosing.

Sensitivity to methacholine is a metric used to test for delayed airway hypersensitivity. In 4 patients, rhLF provided substantial protection against delayed airway hypersensitivity as measured by the provocative concentration of methacholine required to produce a 20% drop in $FEV_1$. Twenty-four hours after pre- and post-treatment allergen challenges, patients were tested for sensitivity to methacholine. Methacholine was administered in increasing incremental doses every 10 minutes until a 20% drop in $FEV_1$ was observed. Protective effect was defined as achieving an increase of at least 1 doubling-dose concentration of methacholine to produce a 20% drop in $FEV_1$ post-treatment. The results presented in Table 3 demonstrate that rhLF provided substantial protection against delayed airway hypersensitivity after 3 days of drug treatment.

TABLE 3

| Patient | Cum Methacholine Dose (mg/ml) Administered 24 h after Allergen Challenge | |
|---|---|---|
| | Pre-Treatment | Post-Treatment |
| 4 | 2.6 | 9.8 |
| 6 | 6.5 | 78.1 |
| 09* | 4.0 | 2.5 |
| 13 | 1.5 | 2.3 |
| Average | 3.7 | 23.2 |

*Patent was non-compliant with dosing.

Example 9

Allergen Challenge Clinical Trial in Atopic Volunteers with Extended rhLF Dosing Atopic patients with a documented response to the allergen are enrolled in a challenge trial. Patients have mild or moderate asthma and are free of other cardio-respiratory illnesses that may interfere with either the safety or the measurement of the early or late asthmatic responses.

Baseline measures of pulmonary function, including $FEV_1$ at 5, 10 and 15 minutes are made before and after inhalation of saline. Baseline allergen response is obtained by administering increasing amounts of known allergen until a fall in $FEV_1$ of 25% is observed. $FEV_1$ is measured at the following times post-allergen inhalation: 20, 30, 45 and 60 minutes. Following this, measurements are made at hourly intervals up to 4 hours, and then every 30 minutes up to 9 hours to untreated allergic response.

The baseline measurement is repeated two weeks after the first measurement.

After a further two weeks, rhLF is administered once a day in doses of 0.1, 0.5, 1.5, 3.0 and 4.5 g/day for fifteen days. On the fourteenth day, a baseline $FEV_1$ is measured prior to allergen exposure. Two hours following the rhLF dose, allergen is administered to the patient in an amount required to decrease the $FEV_1$ by 25%. $FEV_1$ is measured at the following times post-allergen inhalation: 20, 30, 45 and 60 minutes. Following this, measurements are made at hourly intervals up to 4 hours, and then every 30 minutes up to 9 hours to untreated allergic response.

Blood is collected from the patients at baseline and daily for fourteen days following the start of rhLF administration to measure circulating CD4+, CD8+, and NK cells, NK cell activity and serum cytokines including IL-1, IL-2, IL-4, IL-5, IL-8, IL-10, IL-12, IL-18 and IFN-gamma.

Example 10

Clinical Trials in Asthmatic Patients

Patients suffering from mild, moderate or severe asthma are randomly received either placebo, or daily doses of oral rhLF.

Thirty patients with moderate persistent asthma will be randomized and treated. After a 2-week baseline period during which patients must exhibit symptoms of asthma, patients will be randomized to receive either rhLF 3.0 g or placebo twice daily for 4 weeks. After a 2-week wash-out period, patients will be crossed over to the other study drug for an additional 4-week treatment period. All patients will have a follow-up visit performed 4 weeks after completion of both treatment periods.

The primary objective will be to assess the effects of oral rhLF on bronchial hypersensitivity in mild to moderate asthmatics as measured by the methacholine challenge test.

The secondary objective of the study will be as follows: to determine the effects of rhLF on other clinical and laboratory measures of asthma and inflammation [e.g., AM, PM PEF, and PEF variability; nocturnal asthma symptoms; use of rescue medications; spirometry indices;bronchial/bronchial cellularity and cytokine profiles in exhaled breath condensate; exhaled nitric oxide; serum C-reactive protein; serum changes in cytokine profiles (e.g., IL-5, IL-10)] and to determine the safety and tolerability of rhLF administered orally at 3.0 g bid for 28 days in patients with moderate asthma.

Example 11

Combination Therapy in Patients with Asthma, Sinusitis and Allergic Rhinitis

Patients suffering from asthma, sinusitis and allergic rhinitis are administered standard or published anti-asthma, anti-sinusitis or anti-rhinitis regimens respectively with or without the addition of oral rhLF. rhLF is administered using regimens identified as being optimal in the trials described in Example 5. Anti-allergic rhinitis or anti-sinusitis therapy is administered using standard or published regimens.

The efficacy of individual and combination treatments are evaluated by measuring immediate and late phase airway resistance, and delayed hypersensitivity and BAL cellularity as described in Example 1. Yet further, the levels of CD4+, CD8+ and NK cells are counted from the blood that was collected. Plasma, serum and an extract of the blood cells are used for cytokine ELISA assays, i.e., IL-18, IL-1, IL-2, IL-4, IL-5, IL-10, IL-12 and IFN-gamma. Other clinical responses may also be measured, i.e., quality of life scores, eye symptoms, daytime nasal symptoms, nighttime nasal symptoms, etc. (Meltzer et al., 2000; Lindbaek et al., 1996).

Example 12

Multiple Day Oral Administration of Lactoferrin and EDTA

Allergic sheep were selected which demonstrated both early and late-phases asthmatic responses to *Ascaris suum* allergen. Historic control curves for these dual-response sheep were used as the primary experimental controls.

As a negative control for EDTA, allergic sheep were treated with 0.5 mg of EDTA and compared to their historic control in order to confirm that the observed effects were not due to EDTA alone.

Allergic sheep were treated with rhLF and compared to their historic controls. Baseline bronchoalveolar lavage fluid (BAL) samples were taken from all animals and baseline dose response curves to aerosol carbachol were obtained in all sheep 1-3 days before the start of dosing. Next, sheep were pre-treated with either 500 mg oral recombinant human lactoferrin (rhLF), once daily for three days or a combination of 500 mg oral rhLF mixed with 0.5 mg EDTA, once daily for 3 days prior to allergen challenge.

On the challenge day (day 4) the active sheep received either 500 mg oral rhLF or a combination of 500 mg oral rhLF mixed with 0.5 mg EDTA 8 hours after allergen challenge.

On the challenge day (day 4) measurements of lung resistance (RL) were obtained before and then repeated 30 min after treatment and then the sheep were challenged with Ascaris suum allergen using an esophageal balloon catheter (Abraham et al., 1983). Measurements of RL were obtained immediately after challenge, hourly from 1-6 h after challenge and on the half-hour from 6 ½-8 h after challenge. Measurements of RL were obtained 24 h after challenge followed by the 24 h post challenge dose response curve. Airway responsiveness, defined as the cumulative carbachol dose required to increase RL by 400% (Abraham et al., 1983) was measured subsequent to the final dose of lactoferrin or vehicle. Airway resistance of each treated sheep was compared with the control (animal that only received vehicle).

FIG. 8, FIG. 9, FIG. 10, and FIG. 11 show that oral administration of rhLF in combination with EDTA inhibited the late response and airway hypersensitivity more effectively than lactoferrin alone or EDTA alone.

Example 13

Multiple Day Oral Administration of Lactoferrin in Non-Human Primate

Allergically sensitized non-human primates (Cynomolgus monkey's) were treated with rhLF and compared to their historic controls.

Non-human primates were pre-treated with either 250 mg or 100 mg rhLF, orally once a day for 14 days prior to allergen challenge.

On challenge day, the animals were anesthetized and were administered nebulized allergen (aerosolized dust mite) through an endotracheal tube. Pulmonary function was monitored every 30 minutes for 6 to 8 hours to establish the time-course of the late phase response in each animal. While the animals were still under anesthesia, the airways were lavaged. The bronchoalveolar lavage fluid was used to assess inflammatory cell recruitment to the airways following allergen challenge.

Figure 12:
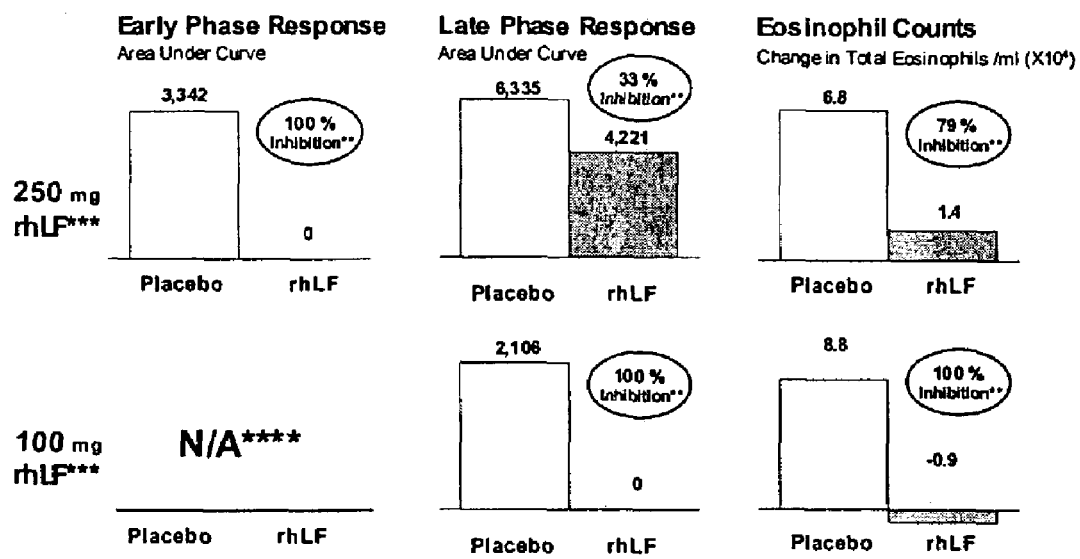
FIG. 12 shows the inhibition of early and late responses, measured as area under curve for lung resistance and the inhibition of eosinophil infiltration for oral administration of recombinant human lactoferrin once daily for 14 days in a non-human primate.

FIG. 12 demonstrates that the administration of liquid oral rhLF inhibited the early and late responses as well as eosinophil infiltration into the airways.

Example 14

Oral Administration of Enterically-coated Lactoferrin in Non-Human Primate

Non-human primates are pre-treated with a dose of rhLF between 1 and 100 mg/kg, orally once a day for 14 days prior to allergen challenge. The rhLF is administered in an enterically coated capsule. Prior to delivery of rhLF, fasting pH of the gastric fluid is measured in order to optimize coating of the capsules. The enterically coated capsules loaded with radio-opaque barium sulfate are delivered to the animals, and transit through the stomach monitored by fluoroscopy to insure delivery and dissolution in the small intestine.

The following parameters are measured: determination of sensitivity to aerosolized histamine and differential cell counts in bronchoaleolar lavage fluid (BAL); measurement of early and late airway responses; and repeat determination of sensitivity to aerosolized histamine and differential cell counts in BAL.

Example 15

Mechanistic Study of rhLF in a Mouse Model of Allergic Asthma

An established mouse model of asthma is used to determine the mechanism of action of rhLF.

Firstly, the mice are administered various doses of rhLF or a placebo for a control and the airway response in allergen challenged mice is observed. This determines the dose of rhLF that produces the maximal protection against airway inflammation and hypersensitivity.

After having established the optimal dose of rhLF, mice are treated again with a standard allergen challenge and the following parameters are measured: cytokine analysis (ELISA and RT-PCR) on the serum, BAL, lung digests and small intestinal digests; histopathology of the lungs to examine cellular infiltration (total and differential), mucous accumulation and exudates; RPA of BAL cells and lung digests; and recall responses of granulocytes isolated from intestine, blood, and lung.

Example 16

Clinical Trial with Oral rhLF as a Treatment for Chronic Sinusitis

Thirty two adult patients with chronic or recurrent sinusitis with or without polyposis who clinically require bilateral endoscopic ethmoidectomy (excluding middle turbinectomy) are admitted to this study. None of the patients have had previous sinus surgery.

Patients are randomized in groups of four to receive either orally rhLF (3 g b.i.d.) or placebo for two months. All patients receive post-treatment antibiotics (either a second generation cephalosporin or clarithromycin) as selected by the investigator for 10 days, analgesic medications as required, and a saline solution spray. Inhaled nasal steroid sprays are not administered. Each patient is seen at weekly intervals for the first 5 weeks. Patients separately indicate the levels of both pain and congestion at each visit on a featureless 100 mm Visual Analog Scale (VAS).

The primary efficacy endpoint is the grade of synechiae and middle meatal stenosis observed between the treated and untreated sinus cavities. Secondary efficacy endpoints include mucosal status, mucosal regeneration, VAS pain scores and the presence of purulent exudates.

Example 17

Clinical Trial with rhLF as a Treatment for Chronic Rhinitis

To evaluate the clinical benefit of rhLF for treating chronic rhinitis, 30 patients are enrolled in a randomized, double-blind, placebo- and active-controlled study. Subjects are nonsmoking outpatients aged 15 to 85 years with chronic rhinitis as demonstrated by positive skin test to allergen and predefined daytime nasal symptoms After a 3- to 5-day placebo run-in period, patients are randomly assigned to treatment with a dose of oral rhLF (n=10) or placebo (n=10) once daily at bedtime for 2 weeks. During the run-in and treatment periods, symptoms are evaluated in a daily diary using a 0 (best) to 3 (worst) scale. During the study patients are withheld from any concomitant medications to treat rhinitis such as corticosteroids or lortadine.

The primary efficacy endpoint are daily symptom scores as recorded in a daily patient diary. Secondary efficacy endpoints include including nighttime symptom scores, daytime eye symptoms, patient and physician global evaluations of allergic rhinitis, and rhinoconjunctivitis quality of life scores. Patients are monitored for safety and any adverse effects are recorded.

Example 18

Effect of Oral Administration of rhLF on GM-CSF in vivo

Recombinant human lactoferrin or placebo were orally administered to mice, and the production of GM-CSF in the small intestine was measured.

Mice (5 animals per group) were treated for three days daily with 300 mg/kg/day of rhLF. For a control, mice were only administered the pharmaceutical carrier. Twenty-four hours following administration of the LF or placebo for 3 days, animals were and the small intestinal tissue was removed for further analysis. Small intestinal epithelium was homogenized using a lysis buffer consisting of PBS, 1% Nonidet P-40, 0.5% sodium deoxycholate, and 0.1% sodium dodecyl sulphate containing 10 µg/ml PhenylMetheylsulfonyl fluoride. Homogenate was centrifuged at 15,000 rpm for 10 minutes and the supernatant stored at −80 C till it was tested for GM-CSF levels using an ELISA kit.

As shown in Table 4, treatment with rhLF increased the production of a key immunostimulatory cytokine, GM-CSF, in the small intestine relative to the placebo treated animals.

TABLE 4

Effect of rhLF on GM-CSF levels in the gut and serum

|  | Mean (SEM) in pg | Increase over Placebo |
|---|---|---|
| Placebo | 6.48 (0.32) | — |
| 300 mg/kg rhLF | 7.74 (0.19) | 19.4% (p < 0.01) |

Example 19

Effect of Oral Administration of rhLF or bLF on IL-18 in vivo

Recombinant human lactoferrin and bovine lactoferrin were orally administered to mice, and the production of IL-18 in the small intestine was measured.

Mice were treated for three days daily with 65 mg/kg/day of rhLF, 300 mg/kg/day of rhLF or 300 mg/kg/day of bLF. For a control, mice were only administered the pharmaceutical carrier. Twenty-four hours following administration of the LF or control for 3 days, animals were weighed and blood and serum were collected. Serum was used for cytokine ELISA assays.

Also, at these time points, animals were sacrificed and the small intestinal tissue was removed for further analysis. Small intestinal epithelium was homogenized using a lysis buffer consisting of PBS, 1% Nonidet P-40, 0.5% sodium deoxycholate, and 0.1% sodium dodecyl sulphate containing 10 µg/ml PhenylMetheylsulfonyl fluoride. Homogenate was centrifuged at 15,000 rpm for 10 minutes and the supernatant stored at −80 C till it was tested for IL-18 levels.

As seen in Table 5 and Table 6, administration of rhLF at both doses significantly enhanced the amounts of IL-18 in both the serum and in the intestinal extract. Bovine LF caused a lesser increase in the intestinal IL-18 levels and did not increase the serum levels of IL-18.

TABLE 5

Effect of rhLF and bLF on IL-18 levels in the gut and serum

|  | Intestinal Extract (pg) | Serum (pg) |
|---|---|---|
| Control | 955 | 141 |
| 300 mg/kg bLF | 4,515 | 134 |
| 65 mg/kg rhLF | 7,879 | 259 |
| 300 mg/kg rhLF | 8,350 | 328 |

TABLE 6

Stimulation by rhLF and bLF of IL-18 levels in the gut and serum

|  | Intestinal Extract % Increase | P-value | Serum % Increase | P-value |
|---|---|---|---|---|
| Increase Over Control |  |  |  |  |
| −300 mg/kg bLF | 373% | 0.0086 | −5% | 0.5411 |
| −65 mg/kg rhLF | 725% | 0.0034 | 84% | 0.0132 |
| −300 mg/kg rhLF | 775% | 0.0001 | 132% | 0.0007 |
| Increase Over Blf |  |  |  |  |
| −65 mg/kg rhLF | 75% | 0.1490 | 94% | 0.0366 |
| −300 mg/kg rhLF | 85% | 0.0617 | 145% | 0.0084 |

Example 20

Effect of Oral rhLF on NK Activity in vivo

Balb/c naïve mice were treated orally with rhLF or placebo once a day for 3 days (see Table 7).

TABLE 7

| | | Treatment Regimen | | | |
|---|---|---|---|---|---|
|  | Treatment* | N | Dose (mg/kg) | Route | Schedule |
| Group 1 | Placebo | 6 | 0 | — | — |
| Group 2 | RhLF | 7 | 300 mg/kg/day | Oral | 3 days |

On day 4, mice were sacrificed and spleens were collected. NK cells were separated using a magnetic bead cell sorting assay (MACS anti-NK-DX5) and counted. Cells were then tested in vitro for NK-activity against YAC targets using a lactate dehydrogenase (LDH) release test.

Table 8 shows that oral rhLF treatment resulted in a significant increase of NK activity ex-vivo against YAC-target cells (10%@30:1 versus 2.8% of ctrl group). No significant change in NK activity was observed in placebo treated mice.

TABLE 8

NK activity in mice treated with oral rhLF

| | Control | | | | | | |
|---|---|---|---|---|---|---|---|
| | Low 0.056 | Medium 0.09 | High 0.407 | | | | |
| | | | Placebo | | RhLF-treated | | |
| | Raw data | | | | Raw data | | |
| E:T ratio | E:T cell mix | E cell ctrl | % Cytotoxicity* Final | | E:T cell mix | E cell ctrl | Final | Increased over ctrl |
| 30:1 | 0.281 | 0.215 | 2.86 | 0.358 | 0.267 | 9.81 | 7** |
| 15:1 | 0.176 | 0.110 | 2.85 | 0.214 | 0.143 | 4.12 | 1.3 |
| 7.5:1 | 0.117 | 0.054 | 2.21 | 0.131 | 0.074 | 0.44 | 0 |
| 3.7:1 | 0.086 | 0.030 | 0.19 | 0.096 | 0.042 | 0 | 0 |

*% Cytotoxicity = [(Effector:target cell mix − effectors cell ctrl)] − low ctrl/[(high ctrl − low ctrl)] × 100
**$p < 0.05$ ((2-tailed p value)

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,571,691
U.S. Pat. No. 5,571,697
U.S. Pat. No. 5,571,896
U.S. Pat. No. 5,629,001
Abraham et al., *Am. Rev. Respir. Dis.* 1983. 128:839-844.
Busse, *Am. J. Respir. Crit. Car Med.* 2001. 164:512-517.
Elrod et al., *Am J. Respir Cir Care Med.* 1997. 156:375-381.
Krishna et al., *J. Allergy Clin Immunol.* 2001. 107:1039-45.
Lindbaek et al., *BMJ.* 1996. 313:325-329.
Meltzer et al., *J. Allergy Clin. Immunol.* 2000. 105:917-22.

Although the present invention and its advantages have been described in detail, it should be understood that various changes, substitutions and alterations can be made herein without departing from the spirit and scope of the invention as defined by the appended description. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended descriptions are intended to include within their scope such processes, machines, manufacture, compositions of matter, means, methods, or steps.

What is claimed is:

1. A method of treating having asthma comprising the step or steps of administering orally to a subject a lactoferrin composition in an amount sufficient to provide an improvement in the asthma in said subject and administering a metal chelator dispersed in a pharmaceutically acceptable carrier in an amount sufficient to enhance the efficacy of the lactoferrin in the lactoferrin composition for treating asthma.

2. The method of claim 1, wherein said lactoferrin composition is dispersed in a pharmaceutically acceptable carrier.

3. The method of claim 1, wherein said lactoferin is mammalian lactoferrin.

4. The method of claim 3, wherein said lactoferrin is human or bovine lactoferin.

5. The method of claim 1, wherein said lactoferin is recombinant lactoferrin.

6. The method of claim 1 further comprising administering an antacid in conjunction with said lactoferrin composition.

7. The method of claim 1, wherein the amount of the lactoferrin in the composition that is administered is about 1 mg to about 10 g per day.

8. The method of claim 1, wherein the amount of the lactoferrin in the composition that is administered is about 10 mg to about 1 g per day.

9. The method of claim 1, wherein the asthma is selected from the group consisting of atopic asthma-and non-atopic asthma.

10. The method of claim 1, wherein the metal chelator is ethylenediaminetetraacetic acid (EDTA), [ethylenebis (oxyethylenenitrilo)] tetraacetic acid (EGTA), 1,2-bis(2-aminophenoxy)eth-ane-N,N,N',N'-tetraacetic acid (BAPTA), or hydroxyethlene triamine diacetic acid, (HEDTA).

11. The method of claim 10, wherein the metal chelator is EDTA.

12. The method of claim 11, wherein the amount of EDTA that is administered is about 0.01 μg to about 20 g per day.

13. The method of claim 11, wherein the ratio of EDTA to lactoferin in the composition that is administered is from 1:10,000 to about 2:1.

14. The method of claim 1 further comprising administering an anti-asthma therapy selected from the group consisting of mast cell degranulation agents, leukotriene inhibitors, corticosteroids, beta-antagonists, IgE binding inhibitors, anti-CD23 antibody, tryptase inhibitors, and VIP agonists and combinations thereof.

* * * * *